United States Patent [19]

Uthemann

[11] Patent Number: 4,925,786

[45] Date of Patent: May 15, 1990

[54] METHOD OF DETERMINING BLOOD GROUPS BY THE SOLID-PHASE PROCEDURE WITH BLOOD-GROUP SPECIFIC ANTIBODIES OF THE IMMUNOGLOBULIN M. TYPE AND SUPPORT AND KIT FOR CARRYING OUT THE METHOD

[75] Inventor: Horst Uthemann, Frankfurt, Fed. Rep. of Germany

[73] Assignee: Biotest AG, Frankfurt am Main, Fed. Rep. of Germany

[21] Appl. No.: 293,271

[22] Filed: Jan. 4, 1989

[30] Foreign Application Priority Data

Jan. 28, 1988 [DE] Fed. Rep. of Germany ....... 3802452

[51] Int. Cl.$^5$ ..................... G01N 31/00; G01N 33/48; G01N 33/053; G01N 33/53
[52] U.S. Cl. ......................................... 435/7; 436/513; 436/524; 436/548; 436/501; 424/11
[58] Field of Search ............... 436/513, 520, 501, 524, 436/548; 424/11; 435/7

[56] References Cited

U.S. PATENT DOCUMENTS 4,764,465  8/1988  Foung et al. ..................... 435/172.2

OTHER PUBLICATIONS

Beck, et al. Med. Lab Sciences (1984) 41, 324–381.
Sinor, et al Transfusion (1985) 25, 21–23.

*Primary Examiner*—Christine M. Nucker
*Assistant Examiner*—Kaen I. Krupen
*Attorney, Agent, or Firm*—Sprung Horn Kramer & Woods

[57] ABSTRACT

A method of, and support and kit for, determining blood groups by the solid-phase procedure with blood-group specific immunoglobulin-M antibodies. The support is prepared by applying to its surface a solution of the immunoglobulin-M antibodies and simultaneously applying to the surface of the support a suspension of erythrocytes that is being tested, or drying the surface of the support to form a ready-to-use reagent, and subsequently contacting the surface with a suspension of erythrocytes, and determining the blood group just after the contact occurs, the concentration of antibodies being just sufficient to create an irreversible or immobilized coating of antibody molecules on the surface that can specifically attach erythrocytes but insufficient to induce an agglutination reaction.

9 Claims, No Drawings

METHOD OF DETERMINING BLOOD GROUPS BY THE SOLID-PHASE PROCEDURE WITH BLOOD-GROUP SPECIFIC ANTIBODIES OF THE IMMUNOGLOBULIN M. TYPE AND SUPPORT AND KIT FOR CARRYING OUT THE METHOD

BACKGROUND OF THE INVENTION

The invention relates to a method of determining blood groups with blood-group specific immunoglobulin-M antibodies and to a support and a kit for carrying out the method.

The agglutination reaction has, due to its simplicity and wide range of application, become one of the most common methods of determining blood groups in recent decades. One of its essential drawbacks however is that it lacks an objective terminal point that can easily be registered either automatically or visually because the reactions that occur within the dilution series vary in intensity to the extent that weak reactions for example can be incorrectly considered negative.

The ELISA (enzyme-linked immunosorbent assay) has recently been employed to determine blood groups. Although this method is admittedly extremely sensitive, it also has drawbacks in the number of steps it requires and in problems relating to the absorbability of antibody and enzyme by erythrocytes and to interactions with intercellular hemoglobin in solution.

Solid-phase methods have recently been introduced as alternatives to the agglutination reaction and to the ELISA test for determining blood groups in the ABO and Rh systems, for antibody screening and for cross-matching (1: H. L. Moore et al., Transfusion 22, 540 [1982]; 2: H. H. Moore, Transfusion 24, 218–221 [1984]; 3: L. T. Sinor et al., Transfusion 25, 21–23 [1985]; 4: F. V. Plapp et al., A.J.C.P. 82, 719–721 [1984]; 5: M. L. Beck et al., Med. Lab. Sci. 41, 374–381 [1984]; 6: J. M. Rachel et al., 25, 24–26 [1985]; and 7: F. V. Plapp et al., The Lancet [1986], 1465–1466). Common to these methods is that positive reaction patterns are represented by a layer of specifically attached erythrocytes on specially prepared solid phases, whereas negative reactions do not lead to the formation of a solid-phase layer. The varying reaction patterns can be read visually or spectrophotometrically, leading to an objective "yes" or "no."

Solid-phase methods of ABO and Rh determination have previously been carried out by exposing a suitable support, such as microtitration plates made of polyvinyl chloride (2) or polystyrene (3) or membranes of nylon or nitrocellulose (7) to buffer solutions of monoclonal or affinity-purified antibodies for long periods, at least 2 hours (2) for example, for coating, leading to the formation of immobilized, meaning irreversibly attached monomolecular solid-phase layers on the plastic surfaces due to passive adsorption. Excess antibodies are rinsed away and the supports, prepared for use in this way, are available for blood-group serology study. The use of anti-D of the IgG type for Rh determination required the creation of a double solid-phase layer consisting of affinity-purified anti-human-IgG (3 & 5) and anti-D to overcome the distance between the plastic surface and the offered erythrocytes.

Although the solid-phase methods known up to now have considerable advantages over the agglutination and ELISA methods, the preliminary coating of the surface of the support has always been complicated.

OBJECT OF THE INVENTION

The object of the present invention is to provide both a simplified and less complicated method of solid-phase determination of blood groups and means of carrying it out.

This object is attained by the improvement which comprises applying a solution of the immunoglobulin-M antibodies to the surface of the support and simultaneously applying to the surface of the support a suspension of erythrocytes that is being tested, or drying the surface of the support to form a ready-to-use reagent, and subsequently contacting the surface with a suspension of erythrocytes, and determining the blood group just after the contact occurs, the concentration of antibodies being just sufficient to create an irreversible or immobilized coating of antibody molecules on the surface that can specifically attach erythrocytes but insufficient to induce an agglutination reaction.

It has, surprisingly, been discovered that the more or less complicated preliminary coating of the surface of the support can be eliminated if the antibodies are specifically reacting immunoglobulins of the M type because the solid-phase coatings can be applied to the surface of the support simultaneously with the specific immunological attachment of erythrocytes if the IgM antibodies and the erythrocyte suspensions are made available to the surface simultaneously. It is of advantage but not essential to use monoclonal or chromatographically affinity-purified antibodies.

What is especially surprising is how rapidly a sufficient quantity of antibodies will attach to the surface. When antibody concentrations are employed that are no higher than necessary in relation to the dimensions of the particular support surface to create an irreversible or immobilized coating of antibody molecules on the surface, meaning that they are not sufficient to induce an agglutination reaction, and when the specificity is appropriate, cell adhesion will occur immediately once the erythrocyte suspensions have been added, while the support is being centrifuged or within 30 to 40 minutes if it is allowed to stand at room temperature.

Although the tests to be described hereinbelow were carried out with supports in the form of polystyrene microtitration plates, any other type of support or support material used in the known methods described in References 1 through 7 can be employed. Given the dimensions of the wells in commercially available microtitration plates, 10 to 50 μl of a 1:10 to 1:1000 dilution of antibodies in water or in an isotonic sodium chloride solution have been proven appropriate.

The method in accordance with the invention can be employed for example with currently available anti-A, anti-B, anti-AB, anti-D, anti-M, anti-N, anti-Le$^a$ and anti-Le$^b$ immunoglobulin-M antibodies.

Especially appropriate are monoclonal antibodies.

It is unnecessary to dilute the antibodies in a buffer solution as employed in the preparation of solid-phase coatings by for example Moore (1 & 2), Sinor et al. (3), Plapp et al. (4), and Beck et al. (5). The erythrocytes are employed in practical terms in concentrations of for example 0.3 to 3.0% and preferably of 0.5% isotonic sodium chloride solutions. The erythrocytes being investigated can be treated with enzymes before the test is conducted.

Positive reactions exhibit a definite cellular lawn as the result of specific attachment of the erythrocytes by way of the presented antibodies to the walls of the wells in the microtitration plate, whereas negative reactions will be recognized as buttons of sedimented cells on the bottom of the wells. The varying pattern can be evaluated visually or can be automatically scanned and interpreted with a spectrophotometer system, a photometer-computer system for example.

Small quantities of antibodies can be dried to prepare ready-to-use supports, microtitration plates for solid-phase tests for example, that will need only the addition of erythrocyte suspensions, for example. Once the dried-on reagents dissolve, cell attachment will proceed rapidly at the appropriate specificity.

EXAMPLE 1

Dilutions of IgM monoclonal antibodies with anti-A, anti-B, anti-AB, and anti-D specificities in isotonic sodium-chloride solution at ratios of 1:10 to 1:1000 (50 µl each) were pipetted into the (U-shaped) wells of a polystyrene microtitration plate with 0.5% erythrocyte suspensions in sodium chloride (50 µl each). Once they had been sufficiently agitated (in a shaker), the plates were allowed to stand at room temperature for 30 minutes.

Positive reactions were indicated by a lawn of cells over the surface of the wells whereas buttons of sedimented cells on the bottom of the wells represented negative results.

EXAMPLE 2

The dilutions employed in Example 1 were dried in the wells. The microtitration plates were then placed in weld-sealed aluminum bags and stored in a refrigerator or at room temperature until used. 50 µl of the 0.5% erythrocyte suspension in sodium chloride were added to each well, and the dried antibodies dissolved when briefly shaken. The plates were allowed to stand as described in Example 1 and read.

EXAMPLE 3

The diluted antibodies and erythrocyte suspensions were contacted and mixed as described in Example 1, and the microtitration plates immediately centrifuged for 1 minute at 1000 r.p.m. and interpreted as described hereinabove.

RESULTS

The results of the method described in Examples 1 through 3 agreed with those obtained from an agglutination reaction 864 times. The new method is accordingly sensitive and can be carried out easily and semi-automatically. $D^u$ bloods were not detected by these methods.

It is understood that the specification and examples are illustrative but not limitative of the present invention and that other embodiments within the spirit and scope of the invention will suggest themselves to those skilled in the art.

What is claimed is:

1. In a method of determining blood groups with blood-group specific immunoglobulin-M antibodies, the improvement which comprises applying a solution of the immunoglobulin-M antibodies to a surface of the support and simultaneously applying to the surface of the support a suspension of erythrocytes that is being tested, and determining the blood group just after the contact occurs, the concentration of antibodies being just sufficient to create an irreversible or immobilized coating of antibody molecules on the surface that can specifically attach erythrocytes but insufficient to induce an agglutination reaction.

2. The method according to claim 1, wherein the antibodies are monoclonal or affinity-purified polyclonal antibodies.

3. The method according to claim 1, wherein the support is microtitration plate.

4. The method according to claim 1, wherein an aqueous or isotonic sodium-chloride solution of the antibodies is employed at a ratio of 1:10 to 1:1000 of antibodies to solution.

5. The method according to claim 3, wherein 10 to 50 µl of antibody solution are added to each well in the microtitration plate.

6. The method according to claim 1, wherein the support is made of polystyrene.

7. The method according to claim 1, wherein the erythrocyte being tested is employed as a 0.3 to 3.0% isotonic sodium-chloride solution.

8. The method according to claim 1, wherein the erythrocyte being tested is employed as a 0.5% isotonic sodium-chloride solution.

9. The method according to claim 1, wherein the blood groups are determined visually or spectrophotometrically.

* * * * *